(12) United States Patent
Long et al.

(10) Patent No.: US 7,915,476 B2
(45) Date of Patent: Mar. 29, 2011

(54) ABSORBENT ARTICLE FOR INTERACTIVE TOILET TRAINING

(75) Inventors: Andrew M. Long, Appleton, WI (US); Christopher P. Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 891 days.

(21) Appl. No.: 11/217,260

(22) Filed: Aug. 31, 2005

(65) Prior Publication Data

US 2007/0049884 A1    Mar. 1, 2007

(51) Int. Cl.
*A61F 13/15*    (2006.01)
*A61F 13/20*    (2006.01)

(52) U.S. Cl. ........................ 604/361; 604/367
(58) Field of Classification Search .............. 604/361, 604/367–378, 385.01
See application file for complete search history.

(56) References Cited

U.S. PATENT DOCUMENTS

| | | |
|---|---|---|
| 4,022,211 A | 5/1977 | Timmons et al. |
| 4,100,324 A | 7/1978 | Anderson et al. |
| 4,663,220 A | 5/1987 | Wisneski et al. |
| 4,704,116 A | 11/1987 | Enloe |
| 4,896,600 A | 1/1990 | Rogge et al. |
| 4,940,464 A | 7/1990 | Van Gompel et al. |
| 5,046,272 A | 9/1991 | Vogt et al. |
| 5,104,116 A | 4/1992 | Pohjola |
| 5,114,781 A | 5/1992 | Morman |
| 5,116,662 A | 5/1992 | Morman |
| 5,197,958 A | 3/1993 | Howell |
| 5,224,405 A | 7/1993 | Pohjola |
| 5,226,992 A | 7/1993 | Morman |
| 5,284,703 A | 2/1994 | Everhart et al. |
| 5,350,624 A | 9/1994 | Georger et al. |
| 5,458,590 A | 10/1995 | Schleinz et al. |
| 5,486,166 A | 1/1996 | Bishop et al. |
| 5,490,846 A | 2/1996 | Ellis et al. |
| 5,508,102 A | 4/1996 | Georger et al. |
| 5,566,616 A | 10/1996 | Schleinz et al. |
| 5,645,542 A | 7/1997 | Anjur et al. |
| 5,649,914 A | 7/1997 | Glaug et al. |
| 5,681,298 A | 10/1997 | Brunner et al. |
| 5,702,376 A | 12/1997 | Glaug et al. |
| 5,766,389 A | 6/1998 | Brandon et al. |
| 5,797,892 A | 8/1998 | Glaug et al. |
| 5,820,973 A | 10/1998 | Dodge, II et al. |

(Continued)

FOREIGN PATENT DOCUMENTS

EP    0 217 032 A2    4/1987

(Continued)

*Primary Examiner* — Michele Kidwell
(74) *Attorney, Agent, or Firm* — Randall W. Fieldhack

(57) ABSTRACT

In a method of a caregiver interactively toilet training a wearer of a disposable absorbent article, in response to liquid insult of the article a tactile signal is perceptible from within the article, a corresponding similar tactile signal is perceptible from an exterior of the article, and an active graphic is visually perceptible at the exterior of the article which relates to both the tactile signal and the corresponding tactile signal to thereby communicate the insult event to the caregiver and provide an interactive toilet training opportunity. An absorbent article of the present invention generally has a tactile signal tactilely perceptible from the inner surface of the article and a corresponding tactile signal tactilely perceptible from the exterior of the article. An active graphic is located adjacent the outer cover and is externally visually perceptible and relates to both tactile signals to provide an interactive toilet training opportunity.

21 Claims, 8 Drawing Sheets

U.S. PATENT DOCUMENTS

| | | | |
|---|---|---|---|
| 5,883,028 A | 3/1999 | Morman et al. | |
| 5,964,743 A | 10/1999 | Abuto et al. | |
| 6,075,178 A | 6/2000 | Wilhelm et al. | |
| 6,231,557 B1 | 5/2001 | Krautkramer et al. | |
| 6,297,424 B1 | 10/2001 | Olson et al. | |
| 6,307,119 B1 | 10/2001 | Cammarota et al. | |
| 6,362,389 B1 | 3/2002 | Mcdowall et al. | |
| 6,552,245 B1 | 4/2003 | Roessler et al. | |
| 6,596,918 B1 | 7/2003 | Wehrle et al. | |
| 6,642,427 B2 | 11/2003 | Roe et al. | |
| 6,645,190 B1 | 11/2003 | Olson et al. | |
| 6,710,221 B1 | 3/2004 | Pierce et al. | |
| 6,958,432 B2 | 10/2005 | Underhill et al. | |
| 2003/0014025 A1* | 1/2003 | Allen et al. | 604/361 |
| 2003/0019374 A1 | 1/2003 | Harte | |
| 2003/0125682 A1 | 7/2003 | Olson et al. | |
| 2004/0087922 A1 | 5/2004 | Bobadilla | |
| 2004/0254549 A1 | 12/2004 | Olson et al. | |
| 2005/0096612 A1* | 5/2005 | Davis et al. | 604/361 |
| 2005/0148961 A1 | 7/2005 | Sosalla et al. | |
| 2006/0004333 A1 | 1/2006 | Olson | |
| 2006/0069360 A1* | 3/2006 | Long et al. | 604/361 |
| 2006/0142713 A1 | 6/2006 | Long et al. | |
| 2006/0142714 A1 | 6/2006 | Jackson et al. | |

FOREIGN PATENT DOCUMENTS

| | | | |
|---|---|---|---|
| EP | 1 216 673 | * | 6/2002 |
| WO | WO 00/37009 A2 | | 6/2000 |
| WO | WO 01/88245 A2 | | 11/2001 |
| WO | WO 02/34184 A1 | | 5/2002 |
| WO | WO 2005/016201 | | 2/2005 |
| WO | WO 2006/014853 A1 | | 2/2006 |
| WO | WO 2006/038932 A1 | | 4/2006 |
| WO | WO 2006/073523 A1 | | 7/2006 |

* cited by examiner

ABSORBENT ARTICLE FOR INTERACTIVE TOILET TRAINING

BACKGROUND OF THE INVENTION

The present invention relates generally to absorbent articles intended for personal wear, and more particularly to such an absorbent article used to interactively toilet train a child.

Disposable absorbent articles find widespread use as personal care products such as diapers, children's toilet training pants and other infant and child care products, adult incontinence garments and other adult care products, sanitary napkins and other feminine care products and the like, as well as surgical bandages and sponges. These articles absorb and contain body waste and are intended to be discarded after a limited period of use; i.e., the articles are not intended to be laundered or otherwise restored for reuse. Conventional disposable absorbent articles comprise an absorbent body disposed between an inner layer adapted for contacting the wearer's skin and an outer layer for inhibiting liquid waste absorbed by the absorbent body from leaking out of the article. The inner layer of the absorbent article is typically liquid permeable to permit body waste to pass therethrough for absorption by the absorbent body.

Disposable absorbent training pants, in particular, are useful in toilet training children. Typically, these disposable undergarments are similar to washable, cloth underwear in the manner in which they are put on and worn, yet provide an absorbent function similar to diapers to maintain skin health. Training pants provide a child undergoing toilet training with an undergarment that eases the transition from diapers to washable, cloth underwear as they become more confident in their ability to use the toilet independently.

In order to learn to use the toilet independently, a child must first learn to recognize when urination has occurred. Because urination may often occur during an activity that distracts the child to the extent that the child does not notice urination, this recognition can represent a substantial hurdle in the training process. Also, a child's ability to recognize when urination occurs may be hampered by the improved performance of disposable absorbent undergarments which quickly draw and retain urine away from the wearer's skin after an insult occurs.

Close monitoring of a toilet-training child by a caregiver can be helpful in that when urination occurs it can be discussed by the child and caregiver to enhance and improve the learning experience. Therefore, it is beneficial to provide the caregiver with immediate notification and/or verification that urination has occurred so that it may be discussed with the child while the event is still fresh in the child's mind.

Several attempts have been made at improving toilet training aids for toilet training pants. For example, training pants that include a temperature change member and/or a dimensional change member which provide a temperature or pressure change sensation to alert the child wearing the pants that urination has occurred have been disclosed. Additional training aids have been used to alert the caregiver and/or child that urination has occurred. Such training aids include disappearing graphics disposed on the outer cover of the pants, audible alarms, vibration sensors, and light indicators that may provide visual or other sensory indication of urination.

Existing training pants having one or more training aids that alert only the wearer, or only the caregiver, to an insult of the pants promote prolonged debates between the child and the caregiver as to whether an accident has occurred. One of the first obstacles to successful toilet training is ending the deniability of the occurrence of an accident by the child. There is a need, therefore, to provide a suitable absorbent article that enhances the toilet training experience for both the child and the caregiver.

SUMMARY OF THE INVENTION

In one aspect of the present invention, a method of a caregiver interactively toilet training a wearer of a disposable absorbent article is disclosed. The method includes providing a tactile signal against the wearer's skin in response to liquid insult of the article, the tactile signal tactilely perceptible from within the interior of the article. A corresponding tactile signal at an outer surface of the absorbent article is provided in response to liquid insult of the article, the corresponding tactile signal being tactilely perceptible from an exterior of the article and being the same type of signal as the tactile signal. The method further includes activating an active graphic in response to liquid insult of the article. The active graphic is visually perceptible at the exterior of the article and relates to both the tactile signal and the corresponding tactile signal to thereby communicate the insult event to the caregiver and provide an interactive toilet training opportunity.

In another aspect of the present invention, there is provided an absorbent article for interactively toilet training a wearer of the article, the absorbent article having an inner surface that faces the article wearer and an outer surface opposite the inner surface. The article includes an outer cover at least in part defining the outer surface of the article, a liner in opposed relationship with the outer cover and at least in part defining the inner surface of the article, and an absorbent structure disposed between the liner and the outer cover. The article further includes a first insult indicator, a second insult indicator, and an active graphic. The first insult indicator comprises a tactile signal tactilely perceptible from the inner surface of the article in response to liquid insult of the article. The second insult indicator is responsive to liquid insult of the absorbent article to provide a corresponding tactile signal tactilely perceptible from the exterior of the article and being the same type of signal as the tactile signal. The active graphic is located adjacent the outer cover, wherein in response to liquid insult of the article the active graphic is visually perceptible at the exterior of the article and relates to both the tactile signal and the corresponding tactile signal to thereby communicate the insult event to the caregiver and provide an interactive toilet training opportunity.

Other features of the invention relate to a temperature or stiffness sensation signal or indicator, and particular configurations for the indicator and the active graphic.

Still other features of the invention will be in part apparent and in part pointed out hereinafter as well as better understood by practice of the invention.

BRIEF DESCRIPTION OF THE DRAWINGS

Corresponding reference characters indicate corresponding parts throughout the drawings.

DETAILED DESCRIPTION

Figure 1:
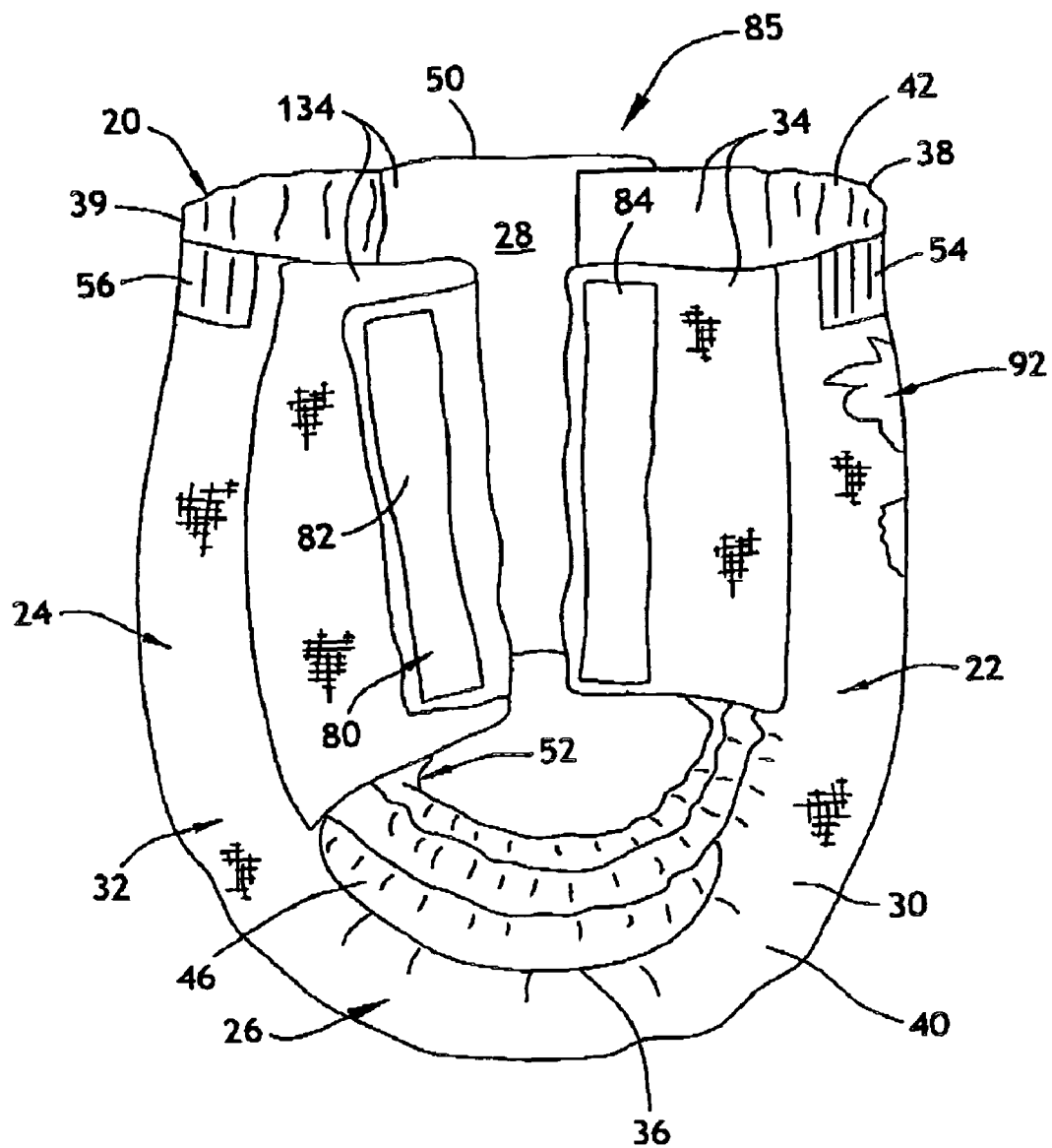
FIG. 1 is a side perspective of an article of the present invention shown in the form of a pair of training pants having a mechanical fastening system fastened on one side of the training pants and unfastened on the opposite side thereof.

Referring now to the drawings and in particular to FIG. 1, an absorbent article of the present invention is representatively illustrated therein in the form of children's toilet training pants and is indicated in its entirety by the reference numeral 20. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference.

Figure 2:
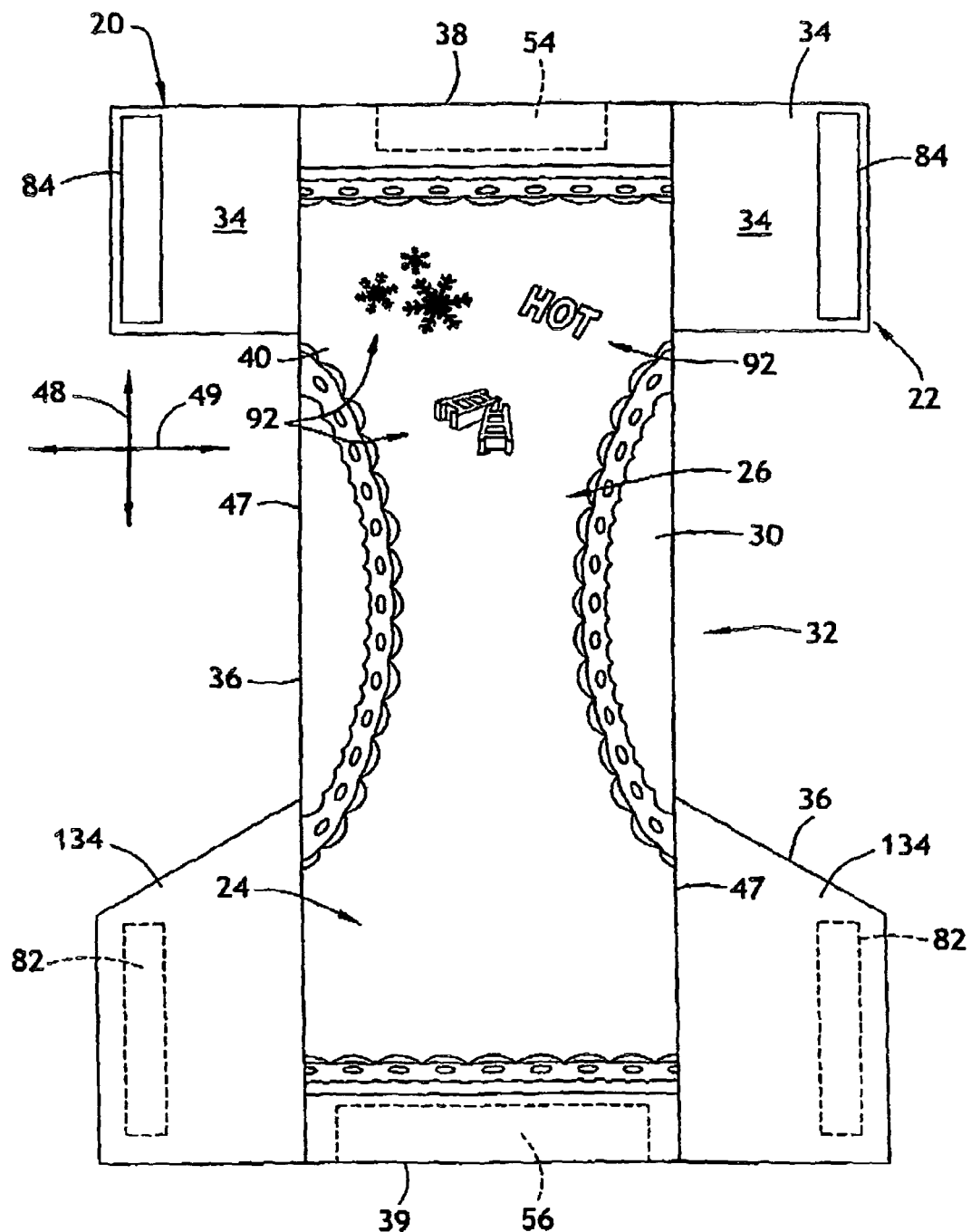
FIG. 2 is a bottom plan view of the training pants of FIG. 1 with the pants in an unfastened, unfolded and laid flat condition, and showing the surface of the training pants that faces away from the wearer and towards a caregiver.
Figure 3:
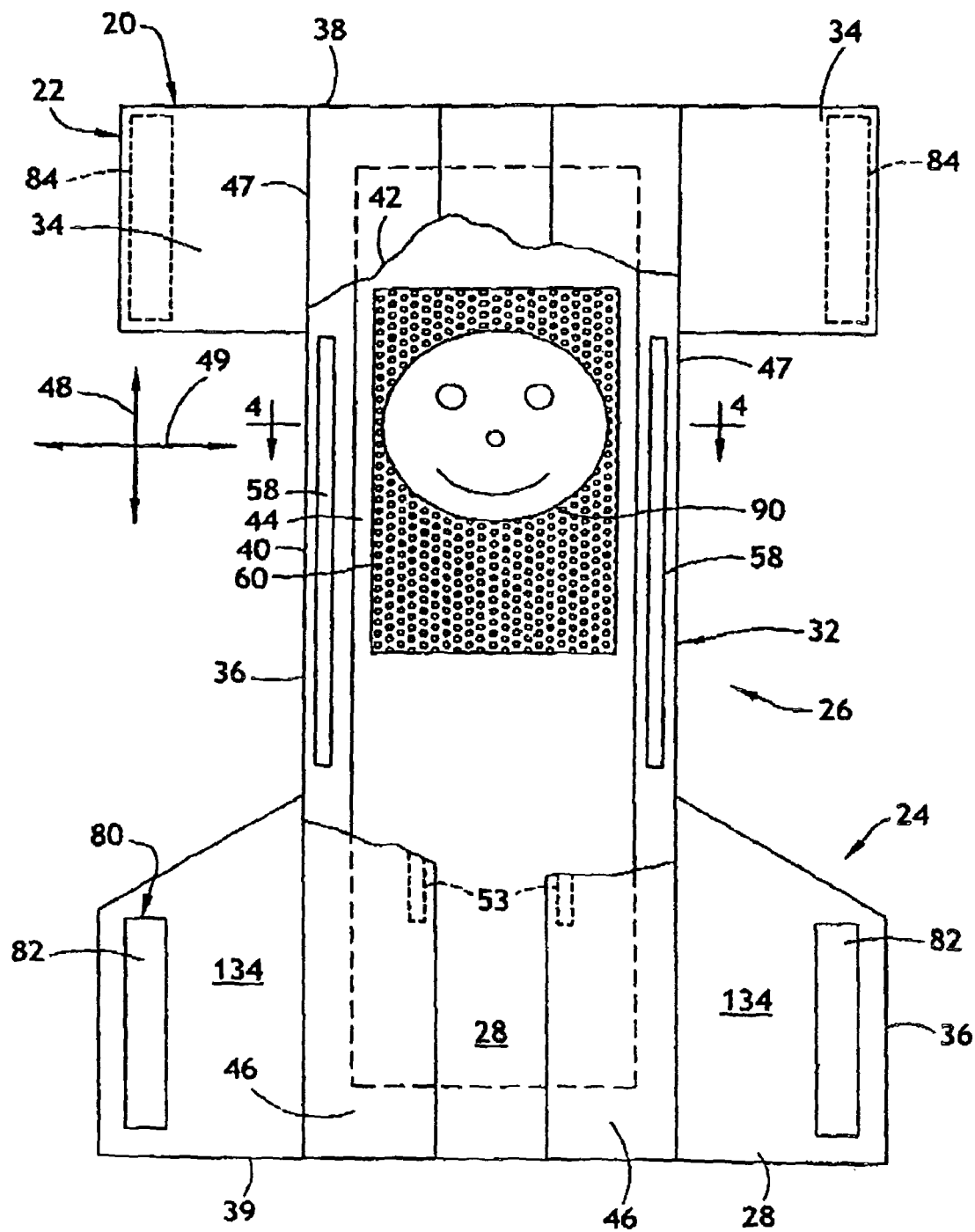
FIG. 3 is a top plan view similar to FIG. 2 showing the inner surface of the training pants that faces the wearer when worn and with portions cut away to show underlying features.

The pair of training pants 20 is illustrated in FIG. 1 in a partially fastened condition. The pants 20 define a longitudinal direction 48 and a lateral direction 49 perpendicular to the longitudinal direction as shown in FIGS. 2 and 3. The pants 20 further define a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The front and back waist regions 22, 24 include those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The pants 20 also define an inner surface 28 adapted in use (e.g., positioned relative to the other components of the pants 20) to be disposed toward the wearer, and an outer surface 30 opposite the inner surface. With additional reference to FIGS. 2 and 3, the pair of training pants 20 has a pair of laterally opposite side edges 36 and a pair of longitudinally opposite waist edges (broadly, longitudinal ends), respectively designated front waist edge 38 and back waist edge 39.

The illustrated pants 20 include an absorbent assembly, generally indicated at 32, and a fastening system for securing the pants in a three-dimensional pants configuration. In the aspect of FIGS. 1-3, the training pants 20 include a generally rectangular central absorbent assembly 32 and side panels 34, 134 formed separately from and secured to the central absorbent assembly. The side panels 34, 134 are permanently bonded along seams 66 to the central absorbent assembly 32 in the respective front and back waist regions 22 and 24 of the pants 20. More particularly, the front side panels 34 can be permanently bonded to and extend transversely outward beyond side margins 47 of the absorbent assembly 32 at the front waist region 22, and the back side panels 134 can be permanently bonded to and extend transversely outward beyond the side margins of the absorbent assembly at the back waist region 24. The side panels 34 and 134 may be bonded to the absorbent assembly 32 using attachment means known to those skilled in the art such as adhesive, thermal or ultrasonic bonding.

The front and back side panels 34 and 134, upon wearing of the pants 20, thus include the portions of the training pants 20 which are positioned on the hips of the wearer. The front and back side panels 34 and 134 can be permanently bonded together to form the three-dimensional configuration of the pants 20, or be releasably connected with one another such as by the fastening system 80 of the illustrated aspects. Suitable elastic materials, as well as one process of incorporating elastic side panels into training pants, are described in the following U.S. patents: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference in their entirety to the extent they are consistent (i.e., not in conflict) herewith. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference in their entirety to the extent they are consistent (i.e., not in conflict) herewith. As is known in the art, the side panels 34, 134 may include elastic material or stretchable but inelastic materials.

The absorbent assembly 32 is illustrated in FIGS. 1-3 as having a rectangular shape. However, it is contemplated that the absorbent assembly 32 may have other shapes (e.g., hourglass, T-shaped, I-shaped, and the like) without departing from the scope of this invention. It is also understood that the side panels 34, 134 may instead be formed integrally with the absorbent assembly 32 without departing from the scope of this invention. In such a configuration, the side panels 34 and 134 and the absorbent assembly would include at least some common materials, such as the bodyside liner 42, outercover 40, other materials and/or combinations thereof.

The absorbent assembly 32 includes an outer cover 40 and a bodyside liner 42 (FIGS. 1 and 3) in a superposed (opposed) relation therewith. The liner 42 can be suitably joined to the outer cover 40 along at least a portion of the longitudinal ends of the pants 20. The liner 42 can be suitably adapted, i.e., positioned relative to the other components of the pants 20, for contiguous relationship with the wearer's skin during wear of the pants. The absorbent assembly 32 also includes an absorbent structure 44 (FIG. 3) disposed between the outer cover 40 and the bodyside liner 42 for absorbing liquid body exudates exuded by the wearer.

With the training pants 20 in the fastened position as partially illustrated in FIG. 1, the front and back waist regions are connected together by the fastening system 80 to define the three-dimensional pants configuration having a waist opening 50 and a pair of leg openings 52. The front and back waist edges 38 and 39 (e.g., longitudinal ends) of the training pants 20 are configured to encircle the waist of the wearer to define the waist opening 50 (FIG. 1) of the pants.

The pants 20 may further include a pair of containment flaps 46 for inhibiting the lateral flow of body exudates. As illustrated in FIG. 3, the containment flaps 46 can be operatively attached to the pants 20 in any suitable manner as is well known in the art. In particular, suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may include a front waist elastic member 54 (FIG. 2), a rear waist elastic member 56, and leg elastic members 58 (FIG. 3), as are known to those skilled in the art. The flap elastic members 53, the waist elastic members 54 and 56, and the leg elastic members 58 can be formed of any suitable elastic material that is well known to those skilled in the art.

The front and back side panels 34 and 134 can be permanently bonded together or be releasably connected with one another such as by the fastening system 80 of the illustrated aspect. The illustrated fastening system 80 includes laterally opposite first fastening components 82 adapted for refastenable engagement to corresponding laterally opposite second fastening components 84. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the pants 20 in its three-dimensional configuration. The fastening components 82, 84 can include any refastenable fasteners suitable for absorbent articles, such as adhesive fasteners, cohesive fasteners, mechanical fasteners, or the like. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

The outer cover 40 may suitably include a material that is substantially liquid impermeable. The outer cover 40 may be provided by a single layer of liquid impermeable material, or more suitably include a multi-layered laminate structure in which at least one of the layers is liquid impermeable. In particular aspects, the outer layer may suitably provides a relatively cloth-like texture to the wearer. A suitable liquid impermeable film for use as a liquid impermeable inner layer, or a single layer liquid impermeable outercover 40 is a 0.025 millimeter (1.0 mil) polyethylene film commercially available from Edison Plastics Company of South Plainfield, N.J. Alternatively, the outer cover 40 may include a woven or non-woven fibrous web layer that has been totally or partially constructed or treated to impart the desired levels of liquid impermeability to selected regions that are adjacent or proximate the absorbent structure. The outer cover 40 may also be stretchable, and in some aspects it may be elastomeric. Reference is made to U.S. Pat. No. 5,883,028, issued to Morman et al., U.S. Pat. No. 5,116,662 issued to Morman and U.S. Pat. No. 5,114,781 issued to Morman, all of which are hereby incorporated herein by reference, for additional information regarding suitable outer cover materials.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable liquid permeable bodyside liner 42 is a nonwoven polyethylene/polypropylene bicomponent web having a basis weight of about 27 gsm; the web may be spunbonded or a bonded carded web. Alternatively, the bodyside liner 42 may also be stretchable, and in some aspects it may be elastomeric. Reference is made to U.S. patent application Ser. No. 09/563,417 filed on May 3, 2000 by Roessler et al., U.S. patent application Ser. No. 09/698,512 filed on Oct. 27, 2000 by Vukos et al., both of which are incorporated by reference herein, for additional information regarding bodyside liner material.

An absorbent structure 44 may be disposed between the outer cover 40 and the bodyside liner 42, which can be joined together by any suitable means such as adhesives, ultrasonic bonds, thermal bonds, or the like. While the illustrated absorbent structure 44 is shown and described herein as extending from the crotch region 26 into both the front and back waist regions 22 and 24, it is contemplated that the absorbent structure may extend from the crotch region into only the front waist region, or only the back waist region, without departing from the scope of this invention.

The absorbent structure 44 can be suitably compressible, conformable, non-irritating to a wearer's skin, and capable of absorbing and retaining liquids and certain body wastes. For example, the absorbent structure 44 may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

The materials may be formed into an absorbent web structure by employing various conventional methods and techniques known in the art. For example, the absorbent structure 44 may be formed by a dry-forming technique, an air forming technique, a wet-forming technique, a foam-forming technique, or the like, as well as combinations thereof. Methods and apparatus for carrying out such techniques are well known in the art. The absorbent structure 44 may alternatively include a coform material such as the material disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. For example, the coform may include materials, or be made by methods, disclosed in U.S. Pat. No. 5,508,102 of Georger et al. issued Apr. 16, 1996, the disclosure of each of which is incorporated by reference herein.

Superabsorbent material may be suitably present in the absorbent structure 44 in an amount of from about 0 to about 90 weight percent based on total weight of the absorbent structure. The absorbent structure 44 may suitably have a density within the range of about 0.10 to about 0.35 grams per cubic centimeter. Superabsorbent materials are well known in the art and can be selected from natural, synthetic, and modified natural polymers and materials.

In one aspect, the absorbent structure 44 may be stretchable so as not to inhibit the stretchability of other components to which the absorbent structure may be adhered, such as the outer cover 40 and bodyside liner 42. For example, the absorbent structure may include materials disclosed in U.S. Pat. Nos. 5,964,743, 5,645,542, 6,231,557, 6,362,389, and international patent application WO 03/051254, the disclosure of each of which is incorporated by reference herein.

In some aspects, a surge management layer (not shown) may be located adjacent the absorbent structure 44 (e.g., between the absorbent structure and the liner 42) and attached to various components of the article 20 such as the absorbent structure and/or the bodyside liner 42 by methods known in the art, such as by adhesive, ultrasonic or thermal bonding. A surge management layer helps to decelerate and diffuse surges or gushes of liquid that may be rapidly introduced into the absorbent structure 44 of the article 20. Desirably, the surge management layer can rapidly accept and temporarily hold the liquid prior to releasing the liquid into the storage or retention portions of the absorbent structure 44. Examples of suitable surge management layers are described in U.S. Pat. Nos. 5,486,166; and 5,490,846. Other suitable surge management materials are described in U.S. Pat. No. 5,820,973. The entire disclosures of these patents are incorporated by reference herein.

Optionally, a substantially liquid permeable wrapsheet (not shown) may surround the absorbent structure 44 to help maintain the integrity of the absorbent structure 44.

The training pants 20 of the present invention include at least two insult indicators (sometimes otherwise referred to as training aids or training elements) that in combination provide an interactive toilet training experience, and when combined with still one or more other training aid can also provide a synergistic toilet training experience. For example, in one aspect the training pants comprises at least one insult indicator that provides a tactile signal (i.e., a signal perceived by a person's sense of feeling, i.e., other than by the skin) to the wearer in response to a liquid insult of the pants, and a corresponding tactile signal and activated active graphic at an exterior of the training pants in response to the liquid insult of the pants. Additionally, the training pants of the invention may include an optional at least one other insult indicator that provides a non-tactile signal (i.e., a signal perceived by one of a person's senses other than feeling, e.g., by the skin) that is perceptible to the wearer and/or to the caregiver.

Generally referring to FIGS. 3 4A and 5-5B, inclusive, the pants 20 comprise at least one insult indicator 60 that provides a tactile signal (e.g., a prolonged temperature change sensation and/or stiffness sensation adjacent to and/or against the wearer's body) that is tactilely perceptible within the interior of the pants upon liquid insult, and at least one insult indicator 61 that provides a tactile signal (e.g., a prolonged temperature change sensation and/or stiffness sensation adjacent to and/or against the outer surface) that is tactilely perceptible from an exterior of the pants, upon liquid insult. The indicator 60 corresponds to the indicator 61 by both providing the same type of signal, e.g., both a temperature change of coolness, or heat, or both, a stiffness sensation. Alternatively, insult indicator 62, seen in FIGS. 5A and 5B, can be used. As such, the first and second insult indicators of the invention are opposing portions of a common structure. The training pants 20 further comprise another insult indicator in the form of exterior active graphic 92. The exterior active graphic 92 is preferably an appearing graphic that provides a signal perceptible at the exterior of the article 20 upon the occurrence of a liquid insult. The training pants of the invention promote a synergistic training effect by providing the external signal in the form of exterior appearing graphic 92 that alerts the caregiver that an insult has occurred and providing related or coordinated exterior tactile and visual signals to the caregiver which correspond to the interior tactile signal provided to the wearer. For example, if indicators 60 and 61 provide a coolness sensation, then active graphic 92 may appear as snow flakes or another symbol associated with coolness. This graphic will invite the caregiver to touch the exterior of the pants and feel the cool sensation, thereby enabling the caregiver to share the child's training experience to provide interactive toilet training. The same holds for blocks (FIG. 2) representing stiffness signal, hot for heat signal, etc., or any other word, symbol or graphic that directs a caregiver's attention to the particular location of the training pants to feel the effect of insult indicator 61 or 62, as applicable.

The insult indicators 60, 61 and 62 of the illustrated aspects can comprise an absorbent pledget disposed between the bodyside liner 42 and the outer cover 40 of the training pants 20. The pledgets 60, 61 and 62 are placed in the crotch region 26 of the article 20 in a position where it is most likely to be contacted with urine. More particularly, for aspects seen in FIGS. 4 and 4A and 9-11, indicator 60 can be located between the bodyside liner 42 and the absorbent structure 44 of the training pants, and indicator 61 can be located between the absorbent structure 44 and the outer cover 40 of the training pants. Alternatively, for aspects seen in FIGS. 5A and 5B, the pledget 62 can be located in a hole in the absorbent structure 44a-d. In this way, the first and second insult indicators are opposing portions of common structure 62 which can save on manufacturing material costs and complexity. Still alternatively, a space 45 can be provided between common structure 62 and the absorbent structure 44c (but also with one or more of 44a, b, and/or d) as desired and more fully taught in US publication document 2004/0254549 published Dec. 16, 2004, 19160 & 20376 which is incorporated herein by reference. Additional space (not shown) like space 45 could be provided between structure 62 and one or more of absorbent structure parts 44a, 44b and/or 44d.

In a particularly suitable aspect, the pledgets 60, 61 and 62 may comprise a coform material having a fluff ratio of at least 65:35 fluff/staple fiber that is apertured and covered with a 0.6 osy (20.4 gsm) highly wettable spunbond material. The coform material resists collapsing of the pledget upon liquid insult (i.e., wetting) to thereby maintain open void space within the pledget. The coform material suitably has a density in the range of approximately 0.15 g/cc to approximately 0.5 g/cc. The pledgets 60, 61 and 62 contains little or no superabsorbent material so that the pledget initially takes in liquid body exudates and retains the liquid for a period of time before the liquid is absorbed by the absorbent structure 44 that may contain a higher amount of superabsorbent particles. The pledget cover material may have a colored tint (e.g., blue) to give a noticeable 3-dimensional appearance to the pledgets 60, 61 and 62. It is contemplated that the pledgets 60, 61 and 62 may comprise only the coform material, e.g., without a cover, or that the cover may be composed of other materials and/or colors without departing from the scope of this invention.

In a particular aspect, the pledget may be sized approximately 6 in. (152 mm) by 2.5 in. (64 mm) and placed approximately 3.75 in. (95 mm) down from the front longitudinal edge margin of the pant 20 and 2.25 in. (57 mm) down from the front longitudinal edge margin of the absorbent structure 44. However, it is understood that the pledget may have other sizes and shapes and be otherwise located in the pants 20.

Figure 6:
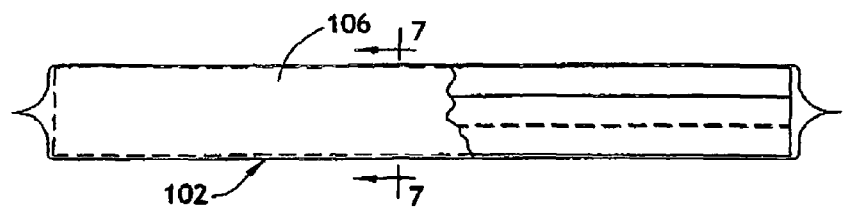
FIG. 6 is an enlarged schematic front elevation of an insult indicator of FIG. 5 with portions partially broken away to reveal internal construction.
Figure 7:
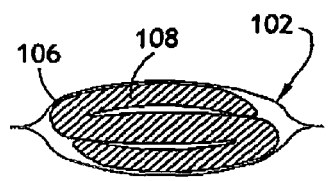
FIG. 7 is a section view taken along the plane including line 7-7 of FIG. 6.

Referring to FIGS. 6-7, there is disclosed a tactile insult indicator in the form of a stiffness sensation member 102 comprising a liquid permeable enclosure 106 having a liquid absorbent body 108 enclosed within the interior of the enclosure. In one aspect, the absorbent body 108 of the insult indicator 102 is a "fan-folded" structure that comprises a sheet material folded over upon itself at least once to form at least two layers that enhances the strength of the absorbent body since each fold layer will act to support adjacent fold layers, further magnifying the expansive pressure within the enclosure 106. Reference is made to co-assigned U.S. patent Ser. No. 10/038,863, filed Dec. 31, 2001 by Olson, et al. and entitled WETNESS INDICATOR FOR ALERTING A WEARER TO URINATION and Ser. No. 10/022,328, filed Dec. 31, 2001 by Underhill et al. and entitled PERSONAL WEAR ARTICLE WITH WETNESS INDICATOR, the entire disclosures of which are incorporated herein by reference, for additional details and alternative constructions of the insult indicator 102.

In use, the insult indicator 102 is generally soft, pliable and cloth-like when dry and has a stiffness generally similar to that of other portions of the pants 20, and more particularly the absorbent structure 44, making the presence of the insult indicator generally imperceptible to the wearer prior to urination. The pliable insult indicator 102 allows the thighs of the wearer to move freely and to readily compress the insult indicator during normal movements. Upon the first insult of liquid body exudates, the insult indicator 102 absorbs liquid, and the absorbent body 108 within the enclosure 106 begins to swell. This swelling of the absorbent body 108 applies a hydraulic pressure against the enclosure 106. The increased stiffness of the insult indicator 102 provides a resistance to bending, folding, creasing, flexing, etc. of the pants 20, particularly in the crotch region 26, that may be readily perceived by the wearer. For example, the increased stiffness may resist movement by the wearer to bring the thighs of the wearer closer together. Such resistance against the inner thighs need not be large, but is suitably sufficient to at least gently resist leg movement of the inside of the legs of the wearer such that the wearer perceives the resistance, which the wearer eventually learns to associate with urination.

The combination of the tactile signal felt by the wearer upon stiffening of the insult indicator 102, for pledget 62 or both pledgets 60 and 61, and the non-tactile signal provided by the exterior active graphic 92 which is visually perceptible at the exterior of the article and relates to both the tactile signal and the corresponding tactile signal, provides the discussed interactive toilet training effect that results in a more beneficial toilet training experience. For example, upon wetting the toilet training pants 20, a child may first feel the effects of the insult indicator 102 and be prompted to check the status of the graphic 92 or otherwise act distracted. At this time, an attentive caregiver who notices the wearer of the pants 20 is uncomfortable or distracted in the pants or experiencing resistance to movement, may discuss with the child that the graphic 92 has appeared (or disappeared as discussed later) and the caregiver can him/her self feel the exterior of the pants to confirm and better identify with the stiffness (or temperature change as discussed next) the child is experiencing (e.g., as provided externally by pledgets 61 or 62, respectively), in an effort to advance the toilet training process. And particularly advantageous, this can all occur without child or caregiver having to touch the inside soiled wet liner of the pant 20, and instead, by touching the dry outer surface of the pants.

Figure 8:
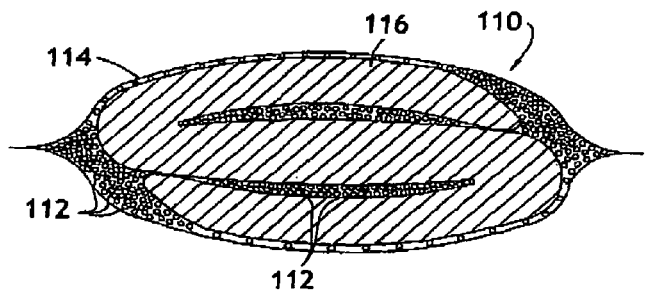
FIG. 8 is cross-section similar to FIG. 7 but showing an alternative second aspect of an insult indicator including temperature change agent.

FIG. 8 illustrates another aspect of a suitable insult indicator 110 similar to the insult indicator 102 of FIGS. 6 and 7 but having a temperature change agent 112 that facilitates a tactile signal (e.g., a hot or cold sensation) against the wearer's body to further alert the wearer that urination has occurred. The temperature change agent 112 is suitably responsive to contact with an aqueous solution, such as urine, to either absorb or release heat. The temperature change can be caused by either an absorption or a release of heat by the temperature change agent 112 to change the temperature of the urine and hence surrounding components of the pants to a temperature noticeable to the wearer. For example, an adsorption of heat by the temperature change agent 112 will provide a cool sensation against the wearer's body (e.g., skin) while a release of heat by the temperature change agent will provide a warm sensation (e.g., warmer than the wearer's skin temperature) against the wearer's body. Reference is made to aforementioned U.S. patent application Ser. No. 10/462,166, incorporated by reference herein, for additional information regarding the mechanism by which the temperature change sensation is accomplished.

In the illustrated aspect of FIG. 8, the temperature change agent 112 is in the form of endothermic material particles, disposed within the liquid permeable enclosure 114 of the insult indicator 110. In use, as urine passes through the liquid permeable enclosure 114 of the insult indicator 110, the urine comes into contact with and dissolves the temperature change agent 112 during or shortly after urination. The temperature change agent 112 absorbs heat from the urine upon dissolution and the cooled urine is then absorbed into the absorbent body 116. The insult indicator 110 may also stiffen upon absorption of the cooled urine, as described previously and apply pressure against the wearer's body, such as against the wearer's inner thighs as described previously. The cooled insult indicator 110 acts in the manner of a heat sink in thermally conductive contact with the wearer's body (e.g., via the liner 42 and/or containment flaps 46 of the pants 20) or just being in proximity to the skin, to thereby draw heat from the wearer and provide a cool sensation to the wearer's body. Positioning the cooled insult indicator in thermally conductive contact with the wearer for a significant duration of time allows the temperature change resulting from the temperature change agent 112 to be more easily noticed by the wearer.

It will be understood that multiple tactile insult indicators (e.g., temperature, stiffness, and the like) may be combined without departing from the scope of this invention. Other examples of suitable tactile sensation indicators are disclosed in co-assigned U.S. Pat. Nos. 5,797,892, 5,702,376 and 5,649,914, the entire disclosures of which are incorporated herein by reference. For example, the swelling and stiffening sensation of the insult indicator 110, in combination with the temperature change sensation, thus facilitate a more direct thermally conductive contact between the cooled insult indicator and the wearer's skin. Use of the stiffening insult indicator 110 to hold the cooled sensation against the wearer's skin reduces the ability of the wearer to escape thermally conductive contact with the heat sink by shifting their body position. It is also contemplated that temperature change agent 112 could be used in training pants without the stiffening insult indicator 110 and remain within the scope of this invention.

Figure 4:
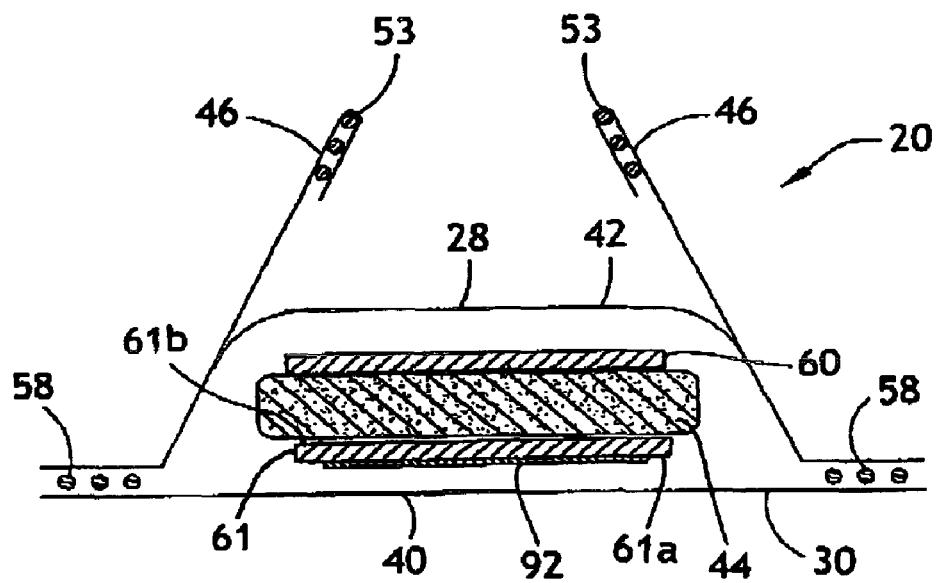
FIG. 4 is a section view taken along the plane including line 4-4 of FIG. 3 showing the placement of a graphic visible from the outer surface of the article.

Referring to FIGS. 3 and 4, active graphic 92 provides a non-tactile signal visible at the exterior of the pants 20 in response to a liquid insult thereof. The active graphic 92 suitably provides a signal that is perceptible, i.e., visible by the caregiver and/or the wearer of the article to confirm that a liquid insult has occurred. As used herein, the term "active graphic" refers to a graphic that visibly (to an unaided human eye) changes appearance in response to a liquid insult of the article. For example, the active graphic may fade or otherwise appear faint following liquid insult (often referred to as a fading graphic), or the active graphic may change from a relatively faint appearance to a bolder, or at least more readily visible appearance (often referred to as an appearing graphic), or the active graphic may change colors in response to a liquid insult.

In the illustrated aspect of FIGS. 3 and 4, the exterior active graphic 92 is suitably an appearing graphic, for example in the form of a symbol related to the tactile signal provided to the wearer and perceptible to the wearer inside the pants and to the caregiver at the exterior of the pants. For instance, the graphic 92 can be a layer of ink suitably disposed adjacent and/or inside the outer cover 40. More particularly, as shown in FIG. 4, the graphic 92 is printed on the top surface 61a of the pledget 61 so that the graphic is visible through the outer cover 40 from the outer surface 30 of the article 20 upon insult. However, it is contemplated that the active graphic 92 may be placed at other locations, or at multiple locations, adjacent the exterior of the pants 20 (e.g., on the cover 40, on the bottom surface 61b of pledget, on the absorbent structure 44, etc.). The graphic may be suitably applied using a flexographic printing process. Flexographic printing apparatus are known to those skilled in art. For example such apparatus are shown and/or described in U.S. Pat. No. 5,458,590 (Schleinz et al.); U.S. Pat. No. 5,566,616 (Schleinz et al.); U.S. 2003/0019374A1 (Harte); and U.S. Pat. No. 4,896,600 (Rogge et al.). Alternatively, the active graphic 92 may be printed, sprayed, or otherwise applied to the absorbent article 20 by another suitable printing method (e.g., ink jet, rotogravure, etc.).

In one aspect, the graphic may be formed from an ink that is soluble in aqueous solutions such as urine. As such, the ink can be positioned in the pants 20 so that it becomes wet and dissolves when the product is insulted with liquid. Suitable urine-soluble inks are available from a variety of commercial vendors, such as Sun Chemical Corp. of Philadelphia, Pa., USA under the trade designation AQUA DESTRUCT. Particular urine-soluble compositions are disclosed in U.S. Pat. No. 4,022,211 issued May 10, 1977 to Timmons et al., which is incorporated herein by reference to the extent it is consistent (i.e., not in conflict) herewith. The ink color can be selected to provide a pleasing appearance and graphic impact, including fading rapidly upon contact with liquid. In particular aspects, and to facilitate rapid fading, the fading graphics can comprise line drawings having a line width of from about 1 to about 5 millimeters.

As another example, in one aspect the exterior active graphic 92 (FIG. 2) suitable for use with the present invention is described in U.S. Pat. No. 6,075,178 issued Jun. 13, 2000 to La Wilhem et al., U.S. Pat. No. 6,297,424 issued Oct. 2, 2001 to Olson, et al., U.S. Pat. No. 6,307,119 issued Oct. 23, 2001 to Cammarota et al., U.S. Pat. No. 6,596,918 issued Jul. 22, 2003 to Wehrele et al., and U.S. Pat. No. 6,710,221 issued Mar. 23, 2004 to Pierce et al., the entire disclosures of which are incorporated by reference herein. It is contemplated that portions of the exterior graphics 92 may be inactive, or permanent graphics as long as other portions of the graphics are active in response to liquid insult of the pants 20.

The exterior active graphic 92 may include, but is not limited to, scenes, characters, animals, objects, alphanumerics such as numbers, letters, words, phrases and the like. In particular aspects, the graphic 92 may also be gender specific, that is, the graphic may be generally considered to be of interest to boys or to girls. It is also contemplated that the exterior active graphic 92 may include portions thereof which are inactive, or permanent, as long as other portions of the graphic are active in response to liquid insult. It is also understood that more than one exterior active graphic 92 may be located within the pants 20 without departing from the scope of the invention. Further reference is be made to U.S. patent application Ser. No. 10/748,411 filed Dec. 29, 2003 and U.S. patent application Ser. No. 10/881,255 filed Jun. 30, 2004, the disclosures of which are incorporated by reference herein, for additional information regarding the placement, composition, and other details and alternatives of the active graphic 92.

In use, the graphic 92 (i.e., the non-tactile insult indicator) visible to the caregiver and/or wearer of the article 20 from the outer surface 30 acts in concert with the insult indicators 60, 61 and 62 (i.e., the tactile insult indicators) to assist in toilet training of the wearer. For example, the child and the caregiver come to recognize that the active graphic 92 changes in appearance whenever the tactile signal against the body is felt. This communicates the insult event to the child and thereby provides an interactive toilet training opportunity that the caregiver can tactilely experience too, an activity which can be key to toilet training and is further aided by a relatively high level of awareness and caregiver involvement. And particularly advantageous, this can all occur without having to touch the inside wet liner of the pant 20 or the wearer having to remove the article 20, which can assist in preventing prolonged debates between the child and caregiver on whether an insult has occurred.

Alternatively, when removal of the training pant is not problematic (i.e., more public areas tending to compromise a trying-to-be-independent child's need for discretion) the interior active graphic 90 also provides the caregiver with other verifiable evidence that liquid insult has occurred, e.g., without having to touch the wet liner of the pants 20, which can also be used to prevent prolonged debates between the child and caregiver on whether an insult has occurred. The interior active graphic 90 can also provide the caregiver with yet another means for relating to the child the relationship between the act of urinating and both the changing of the graphic and tactile signal in the child's pants 20, thereby enhancing the emotional aspects of toilet training.

It is understood that insult indicators other than the insult indicator 60 of FIGS. 3 and 4 may suitably provide a non-tactile signal to the wearer in response to liquid insult of the pants and remain within the scope of the present invention.

Figure 4A:
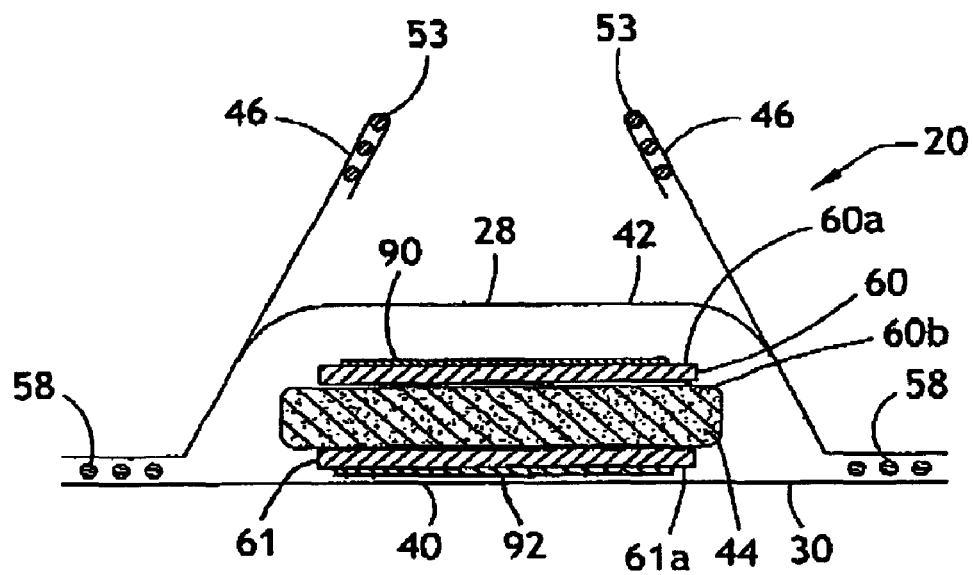
FIG. 4A is a section view similar to FIG. 4 but showing an alternative aspect of the training pants and with an interiorly visible active graphic.
Figure 5:
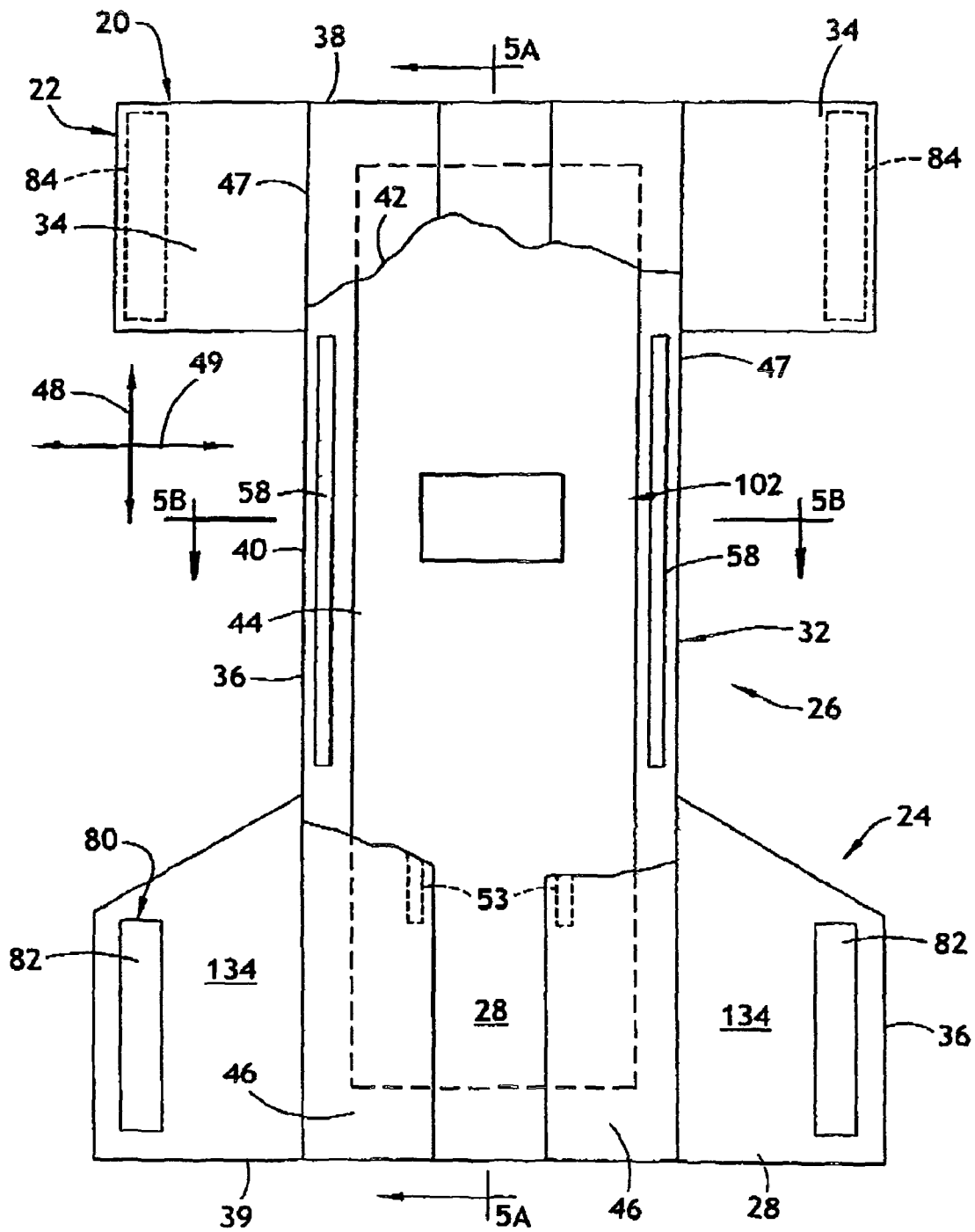
FIG. 5 is a plan view similar to FIG. 3 but showing an alternative aspect of the training pants.
Figure 5A:
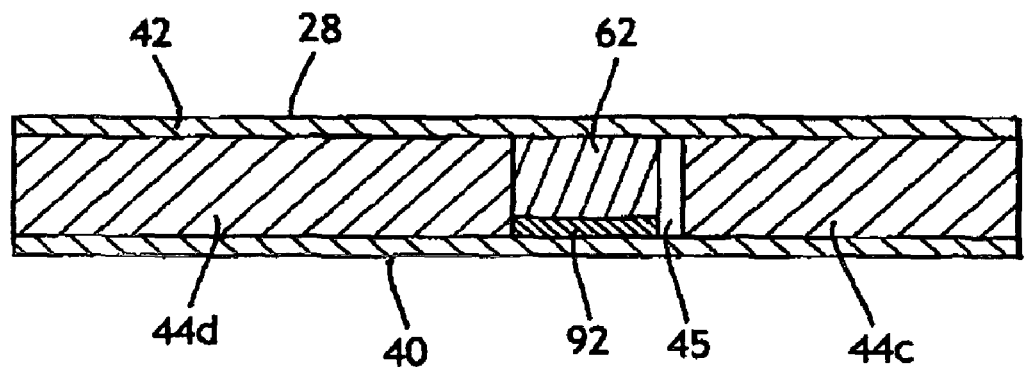
FIG. 5A is a section view taken along the plane including line 5A-5A of FIG. 5.
Figure 5B:
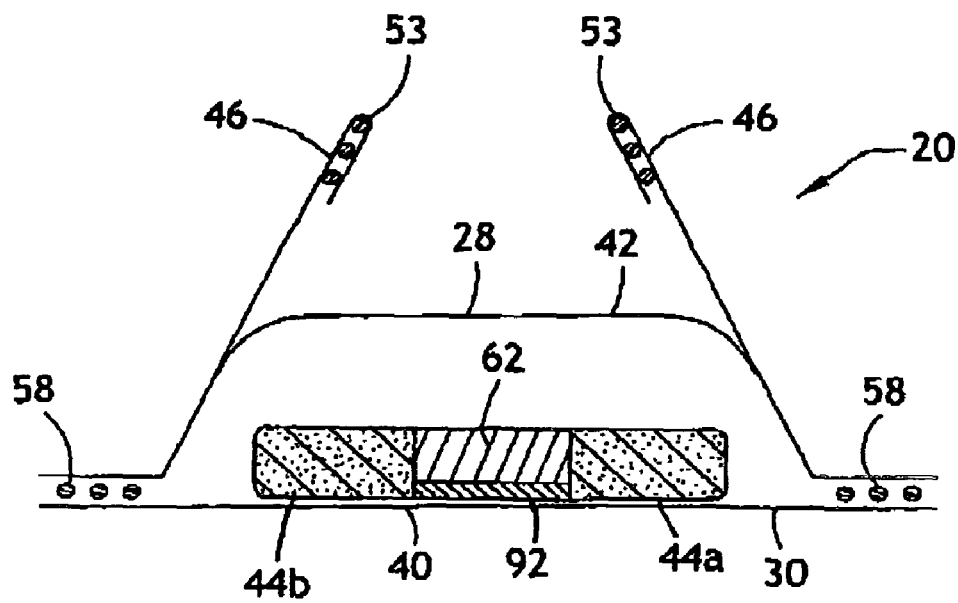
FIG. 5B is a section view taken along the plane including line 5B-5B of FIG. 5.

For example, FIG. 4A illustrates an alternative aspect of the training pants 20 including a non-tactile insult indicator in the form of an interior active graphic 90. Interior active graphic 90 can have some to all of the features just discussed for the exterior active graphic 92. Advantageously, the second active graphic (i.e., interior active graphic) 90 comprises a fading graphic rather than an appearing graphic like exterior active graphic 92. Referring to FIG. 4A, the interior active graphic 90 is printed on the bodyside liner facing surface of the absorbent structure 44 but it is understood that the graphic could be otherwise positioned in the article (e.g., at surface 60a or 60b) as long as the graphic is visible from the interior surface 28 of the article.

It is also contemplated that both interior and exterior graphics 90, 92 may be provided as non-tactile insult indicators. The interior graphic 90 may be related or unrelated to a graphic theme that may be defined by the exterior graphic 92 (FIG. 2). In aspects where the interior graphic 90 is related to a theme established by the exterior graphic 92, it provides an additional opportunity for the wearer and the caregiver to interact and can improve the toilet training experience. For example, in one aspect the theme established by the exterior graphic 92 can include a graphic that cannot complete some action or observation after a fading interior graphic 90 has disappeared. This can be used as a motivational basis for teaching the child that it is within their control to permit the activity to continue for as long as the child can go without wetting his or her pants.

Figure 9:
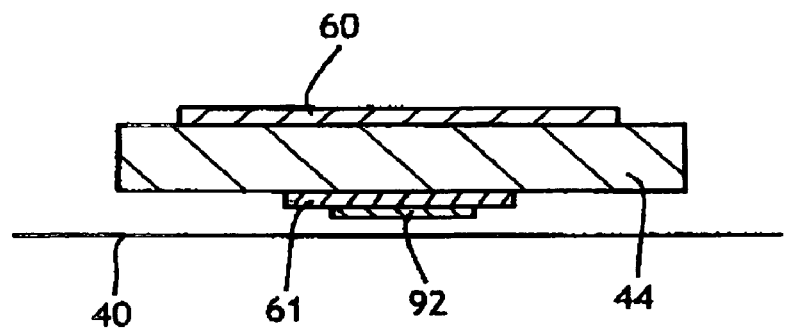
FIG. 9 illustrates a partial section view similar to FIG. 4 but showing an alternative aspect of the absorbent article.
Figure 10:
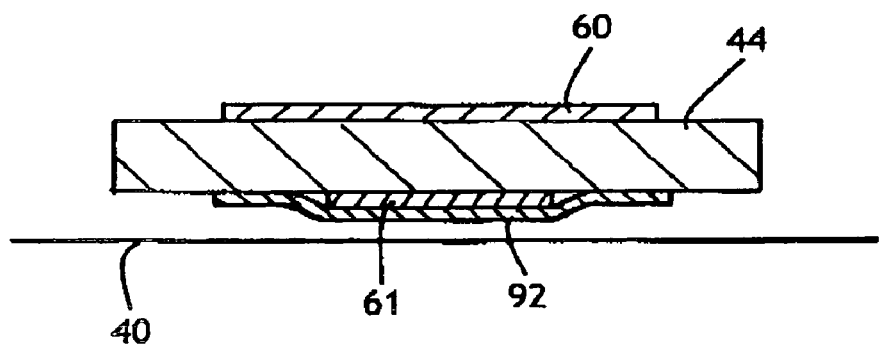
FIG. 10 is a view similar to FIG. 9 but showing another alternative aspect of the absorbent article; and, FIG. 11 is also a view similar to FIG. 9 but showing yet another alternative aspect of the absorbent article.
Figure 11:
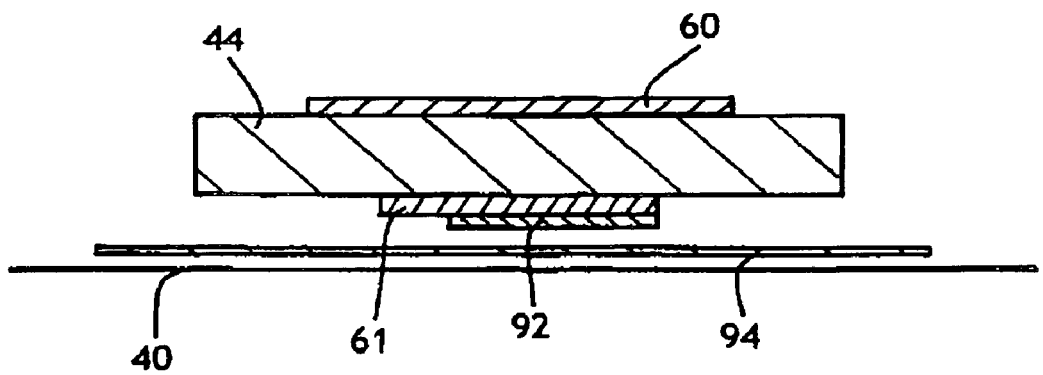

FIGS. 9, 10 and 11 illustrate other alternative aspects of the training pants 20 having a differentially sized exterior active graphic 92 and tactile insult indicators indicated at 60 and 61. The active graphic can be sized and position to at least partially overlay the corresponding insult indicator at the outer surface of the article and thereby direct the caregiver to tactilely evaluate the corresponding tactile signal to enhance the interactive toilet training opportunity. Alternatively, the graphic can be smaller or larger than the exterior insult indicator, and advantageously the active graphic is superposed over the insult indicator (i.e., the graphic lies at or within the perimeter of the insult indicator, as seen in all Figures except 10).

As shown in FIG. 11, yet another feature concerns a protective layer 94 located between the active graphic 92 and the outer cover 40. In this way, if temperature sensitive ink is used for the graphic 92, the layer 94 can act to better ensure the graphic stays hidden until the insult occurs and then the layer changes (e.g., dissolves, becomes transparent, etc.) in response to the liquid insult. Layer 94 can help prevent a false indication of an insult depending on the type and configuration of the active graphic 92. Such a layer 94 could be a film of starch or other well known temporary masking materials.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method of a caregiver interactively toilet training a wearer of a disposable absorbent article having an interior, and exterior, and an outer cover, the method comprising:
providing a tactile signal against the wearer's skin in response to liquid insult of the article, the tactile signal tactilely perceptible from within the interior of the article;
providing a corresponding tactile signal at an outer surface of the absorbent article in response to liquid Insult of the article, the corresponding tactile signal being tactilely perceptible from an exterior of the article through the outer cover and being the same type of signal as the tactile signal; and,
activating an active graphic in response to liquid insult of the article, wherein the active graphic is visually perceptible at the exterior of the article and relates to both the tactile signal and the corresponding tactile signal to thereby communicate the insult event to the caregiver and provide an interactive toilet training opportunity.

2. The method of claim 1 wherein the providing steps each comprise providing a temperature change sensation in response to liquid insult of the article.

3. The method of claim 1 wherein the providing steps each comprise providing a stiffness sensation in response to liquid insult of the article.

4. The method of claim 2 wherein the providing steps each also comprise providing a stiffness sensation in response to liquid insult of the article.

5. The method of claim 1 wherein the interactive toilet training opportunity is provided without the wearer having to remove the article.

6. The method of claim 1 wherein the activating step comprises providing an appearing active graphic in response to liquid insult of the article.

7. The method of claim 1 further comprising activating a second active graphic in response to liquid insult of the article, the second active graphic being visually perceptible from within the interior of the article.

8. The method of claim 1 wherein the activating step comprises positioning the active graphic to at least partially overlay the corresponding tactile signal at the outer surface of the article and thereby direct the caregiver to tactilely evaluate the corresponding tactile signal to enhance the interactive toilet training opportunity.

9. The method of claim 8 wherein the positioning step comprises superposing the active graphic over the corresponding tactile signal.

10. An absorbent article for interactively toilet training a wearer of the article, the absorbent article having an inner surface that faces the article wearer and an outer surface opposite the inner surface, the article comprising:
an outer cover at least in part defining the outer surface of the article;
a liner in opposed relationship with the outer cover and at least in part defining the inner surface of the article;
an absorbent structure disposed between the liner and the outer cover;
a first insult Indicator comprising a tactile signal tactilely perceptible from the inner surface of the article in response to liquid insult of the article;
a second insult Indicator responsive to liquid insult of the absorbent article to provide a corresponding tactile signal tactilely perceptible from the exterior of the article through the outer cover and being the same type of signal as the tactile signal; and
an active graphic located adjacent the outer cover, wherein in response to liquid insult of the article the active graphic is visually perceptible at the exterior of the article and relates to both the tactile signal and the corresponding tactile signal to thereby communicate the insult event to the caregiver and provide an interactive toilet training opportunity.

11. The absorbent article of claim 10 further comprising a second active graphic in response to liquid insult of the article, the second active graphic being visually perceptible from within the interior of the article.

12. The absorbent article of claim 10 wherein the first and second insult indicators each provide a stiffness sensation in response to liquid insult of the article.

13. The absorbent article of claim 10 wherein the first and second insult indicators each provide a temperature change sensation in response to liquid insult of the article.

14. The absorbent article of claim 12 wherein the first and second insult indicators each provide a temperature change sensation In response to liquid insult of the article.

15. The absorbent article of claim 10 wherein at least one of the first and second insult indicators comprise a pledget comprised at least in part of absorbent material and being disposed between the absorbent structure and the liner.

16. The absorbent article of claim 10 wherein at least one of the first and second insult indicators has a first stiffness prior to liquid insult of the article and a second stiffness greater than the first stiffness in response to liquid Insult of the absorbent article.

17. The absorbent article of claim 10 further comprising a protective layer located between the active graphic and the outer cover.

18. The absorbent article of claim 10 wherein the active graphic at least partially overlays the corresponding tactile signal at the outer surface of the article.

19. The absorbent article of claim 18 wherein the active graphic is superposed over the corresponding tactile signal.

20. The absorbent article of claim 10 wherein the first insult indicator and the second insult indicator comprise opposing portions of a common structure.

21. An absorbent article for interactively toilet training a wearer of the article, the absorbent article having an inner surface that faces the article wearer and an outer surface opposite the inner surface, the article comprising:
  an outer cover at least in part defining the outer surface of the article;
  a liner in opposed relationship with the outer cover and at least in part defining the inner surface of the article;
  an absorbent structure disposed between the liner and the outer cover;
  a first insult Indicator disposed between the liner and the outer cover, the first insult indicator comprising a tactile signal tactilely perceptible from the inner surface of the article in response to liquid insult of the article;
  a second insult indicator disposed between the liner and the outer cover, the second insult indicator being responsive to liquid insult of the absorbent article to provide a corresponding tactile signal tactilely perceptible from the exterior of the article through the outer cover and being the same type of signal as the tactile signal; and
  an active graphic located adjacent the outer cover, wherein in response to liquid insult of the article the active graphic is visually perceptible at the exterior of the article and relates to both the tactile signal and the corresponding tactile signal to thereby communicate the insult event to the caregiver and provide an interactive toilet training opportunity.

* * * * *